United States Patent [19]

Poznansky et al.

[11] Patent Number: 5,336,493
[45] Date of Patent: Aug. 9, 1994

[54] SUPEROXIDE DISMUTASE-CATALASE CONJUGATES

[76] Inventors: Mark J. Poznansky, 12 St. Georges Cres., Edmonton, Alberta T5N 3M7; Guo D. Mao, 11055 - 81 Avenue, Edmonton, Alberta T6G 0S2, both of Canada

[21] Appl. No.: 836,274

[22] PCT Filed: Aug. 30, 1990

[86] PCT No.: PCT/CA90/00279
§ 371 Date: Mar. 2, 1992
§ 102(e) Date: Mar. 2, 1992

[87] PCT Pub. No.: WO91/03548
PCT Pub. Date: Mar. 21, 1991

[30] Foreign Application Priority Data

Aug. 31, 1989 [GB] United Kingdom ............. 8919661.2

[51] Int. Cl.⁵ .................. A61K 37/62; A61K 37/50; C12N 9/08; C12N 9/96
[52] U.S. Cl. ................ 424/94.2; 424/94.3; 424/94.4; 435/188; 435/189; 435/192; 530/391.1
[58] Field of Search ............... 435/188, 189, 192, 175, 435/177; 424/85.91, 94.3, 94.4, 94.2; 530/391.1

[56] References Cited

FOREIGN PATENT DOCUMENTS

01/5582 3/1986 European Pat. Off. .
WO89/01033 2/1989 European Pat. Off. .

OTHER PUBLICATIONS

Mao & Poznansky, 1989, *Biomat. Art. Cells & Art. Org.*, vol. 17:3, pp. 229–244.
Chemical Abstracts, vol. 107, No. 3, Abstract 17857k, Jul. 20, 1987.
Chemical Abstracts, vol. 108, No. 25, Abstract 216322c, Jun. 20, 1988.
Chemical Abstracts, vol. 107, No. 8, Abstract 64752g, Aug. 24, 1987.
Chemical Abstracts, vol. 110, No. 15, Abstract 128364d, Apr. 10, 1989.

*Primary Examiner*—Robert A. Wax
*Assistant Examiner*—Keith D. Hendricks
*Attorney, Agent, or Firm*—Lowe, Price, LeBlanc & Becker

[57] ABSTRACT

Novel multi-component conjugates are provided having at least two components which are superoxide dismutase and catalase. Novel therapeutic agents utilising these conjugates are provided which are effective to reduce harmful levels of superoxide and hydroxyl free radicals in body tissues.

7 Claims, 5 Drawing Sheets

SUPEROXIDE DISMUTASE-CATALASE CONJUGATES

TECHNICAL FIELD

This invention relates to novel superoxide dismutase-catalase conjugates and to novel therapeutic agents utilising said conjugates.

BACKGROUND OF THE INVENTION

The human and animal body produces highly reactive free radicals by a variety of normal metabolic processes. The action of xanthine oxidase on xanthine, for example, results in the single-electron reduction of oxygen and produces both superoxide and hydroxyl free radicals (Kuppusamy & Zweier (1989) J. Biol. Chem. 264, 9880–9884). Free radicals have been implicated in the causation of a wide range of clinical conditions including atherosclerosis, rheumatoid arthritis, cancer, pulmonary diseases of the newborn and the normal ageing process, and have been reported to be associated with reperfusion injuries following ischemic episodes associated with myocardial infarct, cerebral ischemia and vasospasm and surgical intervention.

Superoxide and hydroxyl free radicals and hydrogen peroxide can result in peroxidation of membrane phospholipids and oxidation of cellular proteins and nucleic acids. These species are thought to be involved in various pathological conditions including tissue injury, inflammatory conditions and radiation damage.

A variety of endogenous defence mechanisms are thought to protect the organism from the deleterious effects of these reactive oxygen species under normal physiological conditions. One of these is the enzyme, superoxide dismutase (SOD), which occurs widely in prokaryotes and eukaryotes. SOD catalyses the dismutation of the superoxide free radical ($O_2\cdot$), in the presence of hydrogen, to produce hydrogen peroxide.

Hydrogen peroxide, which is itself a potentially deleterious reactive species, is reduced to oxygen and water by the enzyme, catalase. Catalase also destroys the hydroxyl free radical (OH.) by removing $H_2O_2$ and hence decreasing the reaction of $H_2O_2$ with $O_2\cdot$ to produce OH..

The effect of exogenously administered SOD as a therapeutic agent to protect against superoxide free radical damage has been studied in mammals with mixed results. The variability of the effect produced by SOD makes it somewhat unsatisfactory as a therapeutic agent.

One factor contributing to the variability of effect found with exogenous SOD administration is the very short half-life of SOD in the mammalian circulation, of the order of 4 to 5 minutes.

Previous work has shown that the half-life of SOD in the circulation can be increased by conjugation of the enzyme with a larger molecule, for example, albumin or polyethylene glycol (PEG). SOD-albumin conjugates have circulation half-lives of 4–6 hours and show reduced immunogenicity compared to SOD alone (Mao & Poznansky (1989), Biomat. Art. Cells & Art. Org., v. 17 (3), p. 229–244).

Another factor which likely plays a role in the variable results found with exogenous SOD administration is the strong inhibition of SOD by hydrogen peroxide, one of the products of its own catalytic activity.

A further limitation on the usefulness of SOD, and also of SOD-albumin conjugates, is that SOD is not able to remove hydroxyl free radicals. At high levels of exogenous SOD administration, SOD actually increases hydroxyl free radical production and a similar effect is seen with high levels of SOD-albumin conjugate.

The SOD-careless conjugates of the invention are advantageous as novel free radical scavengers capable of removing both oxygen and hydroxyl free radicals.

DISCLOSURE OF THE INVENTION

According to one aspect of the invention, a multi-component conjugate having at least two components is provided, wherein said at least two components are superoxide dismutase and catalase.

According to a further aspect of the invention, a pharmaceutical composition is provided comprising a multi-component conjugate having at least two components, wherein the at least two components are superoxide dismutase and catalase, in an amount effective to reduce harmful levels of superoxide and hydroxyl free radicals in body tissues.

According to a further aspect of the invention, a method of treatment of a subject having a condition in which superoxide and hydroxyl free radicals play a harmful role is provided, said method comprising administration to said subject, in an amount effective to reduce the tissue levels of said free radicals, of a multi-component conjugate having at least two components wherein the at least two components are superoxide dismutase and catalase in a pharmaceutically acceptable carrier.

According to a further aspect of the invention, a method of treatment of a subject is provided to reduce tissue levels of superoxide and hydroxyl free radicals in said subject, said method comprising administration to said subject of an effective amount of a conjugate of superoxide diemurals and catalase in a pharmaceutically acceptable carrier.

The invention, as exemplified by preferred embodiments, is described with reference to the drawings.

MODES OF CARRYING OUT THE INVENTION

Figure 1:
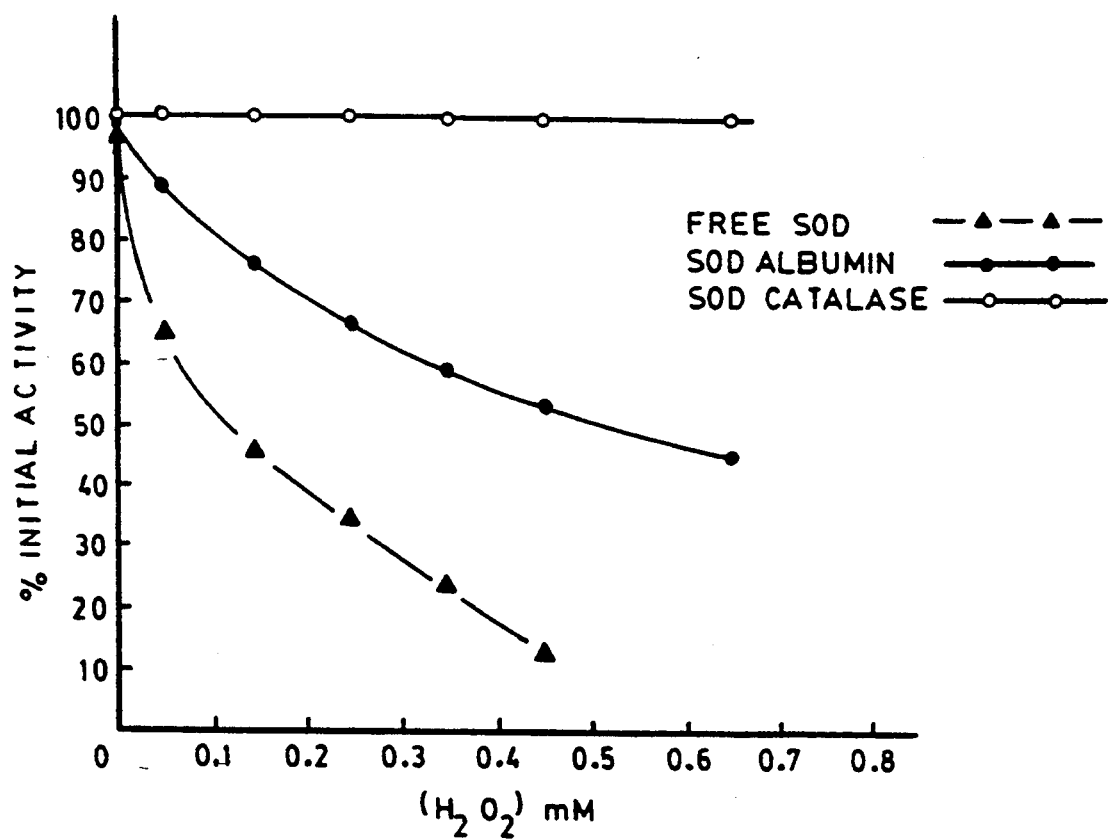
FIG. 1 is a graph showing the percent inhibition of SOD activity at varying concentrations of $H_2O_2$ for SO alone (-▲-), SOD-albumin conjugate (-○-) and SOD-catalase conjugate (-○-).

SOD and catalase are "conjugated", as that term is used herein, when they are attached to each other in such a manner as to resist separation under normal physiological conditions. It is presently preferred to conjugate SOD and catalase chemically, using a divalent linking group such as glutaraldehyde or carbodiimide. However, one may employ any suitable linking group which does not result in loss of enzyme activity to an unacceptable degree. A number of linking groups are commonly used for conjugating antibodies to enzymes used for signal amplification in ELISA methods, and are generally suitable for the practice of the present invention. Alternatively, one may conjugate SOD and catalase indirectly, by conjugating each one, individually or simultaneously, to a macromolecular carrier such as albumin (preferably HSA), polyethylene glycol, starch, and the like. In general, any soluble nonimmunogenic macromolecule should be acceptable as a carrier for conjugates of the invention.

Conjugation need not be covalent: for example, one may conjugate catalase and SOD to individual binding partners which bind by non-covalent interactions. For example, one may conjugate SOD to avidin and conjugate catalase to biotin: conjugates of the invention are then prepared by mixing SOD-avidin and catalase-biotin, and allowing the avidin-biotin affinity to effectively couple SOD and catalase. Other binding partners include receptor-ligand and antibody-antigen pairs, although the avidin-biotin pair is generally the easiest to employ and is the least antigenic.

As used herein, "SOD" refers to superoxide dismutase obtained from any organism, and enzymes exhibiting substantially the same activity. "SOD" also refers to variations on the native enzyme obtained by mutagenesis, recombinant engineering, or other synthetic techniques. SOD derived from a variety of sources is commercially available. Common sources include bovine kidney, bovine liver, canine erythrocyte, horseradish, human erythrocyte, yeast, and bacteria. Similarly, "catalase" refers to any catalase enzyme, obtained from any organism, and variations thereof substantially retaining native catalase activity. Catalase derived from a variety of sources is also commercially available.

"SOD-catalase conjugates" as that term is used herein, may contain components in addition to SOD and catalase, for example albumin or a targeting agent, as described further herein.

General Method

SOD and catalase obtained from commercial sources are suitable for-conjugation. Chemical conjugation may be effected by agents such as glutaraldehyde, which links primary amino groups, and water soluble carbodiimide, which links amino groups to carboxyl groups.

By varying the conjugation conditions, SOD-catalase conjugates of different molecular weights and mole ratios may be prepared.

SOD-catalase conjugates of molecular weights ranging from around 200,000 to around 1,200,000 have been prepared and all were active in scavenging superoxide and hydroxyl free radicals. Conjugates of SOD:catalase mole ratios ranging from 1:1 to 8:1 showed similar free radical scavenging ability. Various methods of conjugating or cross-linking enzymes are described in Poznansky, (1988) in Methods in Enzymology; Ed. K. Mosbach, V. 137, Immobilized Enzymes & Cells, Part D, p. 566.

Genetic engineering techniques may also be used to effect linkage of SOD and catalase to provide cloned quantities of homogeneous conjugates (Bulow & Mosbach, *Ann. N. Y. Acad. Sci.*, 1987, Vol. 501, p.44). Other methods of conjugating SOD and catalase will be known to those skilled in the art.

The SOD-catalase conjugates of the invention retain substantially all of the catalase and SOD catalytic activities of the unconjugated enzymes. Catalase activity may be modestly decreased whereas SOD activity is unaffected or, where glutaraldehyde is used as conjugating agent, somewhat enhanced.

The preservation of enzyme activity on conjugation is shown in Table 1.

TABLE 1

SOD and Catalase Activity Following Cross Linking with either Glutaraldehyde or Carbodiimide

| Enzyme Activity | Enzyme Prep. | % Initial Activity* |
|---|---|---|
| SOD | (SOD-Cat)[1] | 110% |
| Catalase | (SOD-Cat)[1] | 80% |
| SOD | (SOD-Cat)[2] | 100% |
| Catalase | (SOD-Cat)[2] | 72% |

*Enzyme Activity Expressed as a percentage of preconjugation activity.
[1] Conjugation by glutaraldehyde as in Example 1
[2] Conjugation by carbodiimide as in Example 3
SOD activity before and after conjugation was assayed by the method of McCord & Fridovich (1969) J. Biol. Chem., v. 244, p. 6049 and catalase by the method of Claiborne, A. in Handbook of Methods for Oxygen Radical Research (1985) Ed. R. A. Greenwald, CRC Press, p. 283.

The SOD-catalase conjugates of the invention provide novel agents which can destroy both superoxide and hydroxyl free radicals, both of which are cytotoxic. Additionally, the conjugates of the invention provide catalase activity adjacent to the site of $H_2O_2$ production by the action of SOD, thus removing $H_2O_2$ before it can inhibit the SOD or cause peroxidation of cell components. FIG. 1 shows the protective effect of conjugation to catalase on the inhibition of SOD by $H_2O_2$.

Without limiting ourselves to this one theory, one possible mechanism by which the catalase enzyme reduces inhibition of the SOD enzyme is illustrated by the following three equations.

1. Role of SOD in dismutating $O_2^-$:
   $O_2^- + O_2^- + 2H^+ \xrightarrow{SOD} H_2O_2 + O_2$;
2. Role of $H_2O_2$ in producing $\underline{OH}$.:
   $H_2O_2 + O_2^- \longrightarrow OH\cdot + OH^- + O_2$; and
3. Role of Catalase in getting rid of $H_2O_2$ and hence $\underline{OH}$.:
   $2H_2O_2 \xrightarrow{catalase} 2H_2O + O_2$ Other possible mechanisms and theories would be appreciated by those skilled in the art.

Conjugation of SOD with catalase provides an SOD preparation having an extended circulation half-life suitable for therapeutic use. As measured in anaesthetized rate, free SOD has a half-life in the circulation of 4–5 minutes. The SOD-catalase conjugate can remain circulating with a half-life of as much as 5–6 hours dependent on the molecular weight of the conjugate.

Conjugates of SOD, catalase and albumin may be prepared by addition of albumin, preferably human serum albumin, to the pre-conjugation enzyme mixture, giving conjugates of reduced immunogenicity. An SOD-careless-albumin conjugate, prepared as described in Poznansky (Methods in Enzymology, supra), had a molecular weight greater than 600,000 and retained full SOD and catalase activity.

Targeting agents such as antibodies capable of tissue-specific or cell component-specific binding may also be conjugated with SOD and catalase to direct the conjugate to a desired site of action.

A conjugate including SOD, catalase and a monoclonal antibody to heavy chain myosin was prepared as described by Poznansky (Methods in Enzymology, supra). This conjugate showed no loss of SOD or catalase activity and retained the ability of the antibody to bind to its antigen.

The SOD-careless conjugates of the invention effectively remove superoxide and hydroxyl free radicals in the presence of agents such as iron which stimulate production of hydroxyl free radicals. If SOD alone is used in this situation, it has little scavenging effect on hydroxyl free radicals and under some circumstances itself stimulates further production of hydroxyl free radicals.

Due in part to their longer circulation half-life and to the proximity of the catalase portion to the site of $H_2O_2$ production by SOD, the SOD-careless conjugates of the invention are superior to equivalent amounts of unconjugated SOD and catalase in scavenging superoxide and hydroxyl free radicals, as seen in Example 8.

The conjugates of the invention provide useful therapeutic agents for protecting organisms against damage due to superoxide and/or hydroxyl free radicals. In clinical situations involving a period of ischaemia followed by re-perfusion and re-oxygenation, reperfusion injury is common and free radicals have been implicated in such injury. The conjugates of the invention preserve cardiac function in mammalian hearts during re-perfusion following an ischaemic episode whereas unconjugated SOD under similar conditions shows little or no protective effect, as seen in Example 9. The conjugates of the invention provide novel therapeutic agents useful in such clinical situations to inactivate both superoxide and hydroxy free radicals. It will be appreciated by one skilled in the art that an SOD-catalase conjugate could be applied in numerous other clinical situations in which the removal of free radicals is desired.

The extended half-life of the conjugates of the invention in the circulation provides a superior therapeutic agent to the quickly-excluded free SOD.

The conjugates of the invention provide therapeutic agents useful in clinical conditions in which damage is caused by superoxide and hydroxyl free radicals or in clinical situations in which $H_2O_2$ is produced, including situations in which SOD is desirably employed to inactivate superoxide free radicals.

Further details of the preferred embodiments of the invention will be understood from the following examples which are understood to be non-limiting.

EXAMPLES

Example 1

Conjugation by glutaraldehyde 5 mg. SOD (yeast SOD purified to homogeneity (99% by SDS Page), specific activity 5500 U/mg, Sigma) and 2 mg. catalase (porcine liver, specific activity 10,000 U/mg) were dissolved in phosphate-buffered saline, pH 7.4.

100 µl of glutaraldehyde (25%) was added with stirring at 4° C. for 3h. The reaction was stopped by the addition of 50 mg of glycine, the solution was dialyzed overnight against phosphate buffered saline and the product was sized and purified by molecular sieve chromatography using Sephadex G-150 (trade-mark).

On chromatography of the product on Sephadex G-150, 90% of the SOD activity eluted between molecular weights 250,000 and 650,000 with peak activity at 450,000. Profiles of catalase activity and protein content of the eluted fractions were almost identical to the SOD profile.

Rechromatography of the peak fractions on Sephadex G-150 gave a product of molecular weight 450,000±50,000 (mean±1 Standard Deviation).

Recovery of enzyme activity was 110% for SOD and 80% for catalase. Mole ratio of SOD:catalase was 4.

Example 2

Conjugation by Glutaraldehyde

2mg SOD plus 1 mg catalase (activities as in Example 1) were dissolved in 4 ml of phosphate buffered saline (PBS, pH7.4) to which 50 µl of glutaraldehyde was added with stirring for 1h at 4° C. The reaction was stopped as in Example 1 and purification and assay of the conjugate was carried out. These conditions yielded a conjugate with a smaller molecular weight (250,000±40,000) with a mole ratio of 8 (SOD/catalase) and with enzyme activity recoveries of 100% and 75% for the SOD and catalase respectively.

SOD-careless conjugates of different molecular weights or SOD:catalase mole ratios may be prepared by varying the conditions of the cross-linking reaction in terms of the starting mole ratio of unconjugated enzymes, concentration of cross-linking agent and reaction time and temperature, as is known to one skilled in the art.

Example 3

Conjugation by carbodiimide

20 µg water soluble carbodiimide EDCI (1-ethyl-3-(3-dimethylaminopropyl)-carbodiimide HCl) was added with stirring to 2mg SOD dissolved in PBS at 4° C. for 8 hours.

The reaction mixture was dialysed against PBS for a minimum of 4 hours to remove unreacted carbodiimide and catalase (0.5 mg) was added, with continued stirring at 4° C. for 2 hours. Reaction was stopped as in Example 1 and the product was sized and purified as in Example 1.

The purified product had a molecular weight of 600,000 and a mole ratio SOD:catalase of 3.

Example 4

Half-life of SOD-catalase Conjugates

SOD-catalase conjugates were radiolabelled by standard methods and their half-lives were determined in rate anaesthetised with Nembutal.

The radiolabelled conjugate (1 million counts) was injected intravenously with or without a 100 fold excess of unlabelled conjugate. Blood samples were drawn every 30 minutes. The conjugate prepared as in Example 1 had a circulation half-life of 300 minutes compared to the half-life of 5 minutes for the native or unmodified SOD and 120 minutes for the unmodified catalase.

Conjugates examined had half-lives ranging from 60 minutes to 420 minutes depending on the SOD : catalase mole ratio and the molecular weight of the conjugate.

Example 5

Scavenging of Free Radicals by SOD-catalase Conjugates

SOD-catalase conjugate was prepared as in Example 1.

Xanthine and xanthine oxidass were used to generate superoxide free radicals and hydroxyl free radicals, using the system of Fridovich, I., Xanthine Oxidass in: Handbook of Methods for Oxygen Radical Research (1985) Ed. R. A. Greenwald, CRC Press, p. 51.

Free radicals were detected by Electron paramagnetic Resonance (EPR) spin trapping with DMPO as described by Thornalley, P. J. & Bannister, J. V., The Spin Trapping of Superoxide Radicals in Handbook of Methods for Oxygen Radical Research (1985) Ed. R. A. Greenwald, CRC Press, p. 133.

The xanthine (X) plus xanthine oxidass (XO) reaction was allowed to proceed at 37° C. in the presence or absence of free catalase (Cat), free SOD or SOD-catalase conjugates (SOD-Cat). At t=0 or t=10 min, the spin trapping agent DMPO was added and the sample was placed in a Bruker 300 EPO spectrometer.

EPR peaks were scored on an intensity scale of 0–10 and the results are set out in Table 2

TABLE 2

SOD, Catalase and SOD-catalase Mediated Scavenging of Superoxide ($O_2^-$) and Hydroxyl (OH.) Free Radicals

| | | $O_2^-$ | OH |
|---|---|---|---|
| X + XO | t = 1 min | 8 | 1 |
| X + XO | t = 10 min | 10 | 4 |
| X + XO + SOD | t = 1 min | 0 | 1 |
| X + XO + SOD | t = 10 min | 0 | 2 |
| X + XO + SOD − Cat | t = 1 min | 0 | 0 |
| X + XO + SOD − Cat | t = 10 min | 0 | 0 |
| X + XO + Cat | t = 1 min | 8 | 0 |
| X + XO + Cat | t = 10 min | 10 | 2 |

Example 6

SOD-catalase conjugate was prepared as in Example 1.

Xanthine and xanthine oxidass were used to generate superoxide free radicals and hydroxyl free radicals as in Example 5.

Figure 2:
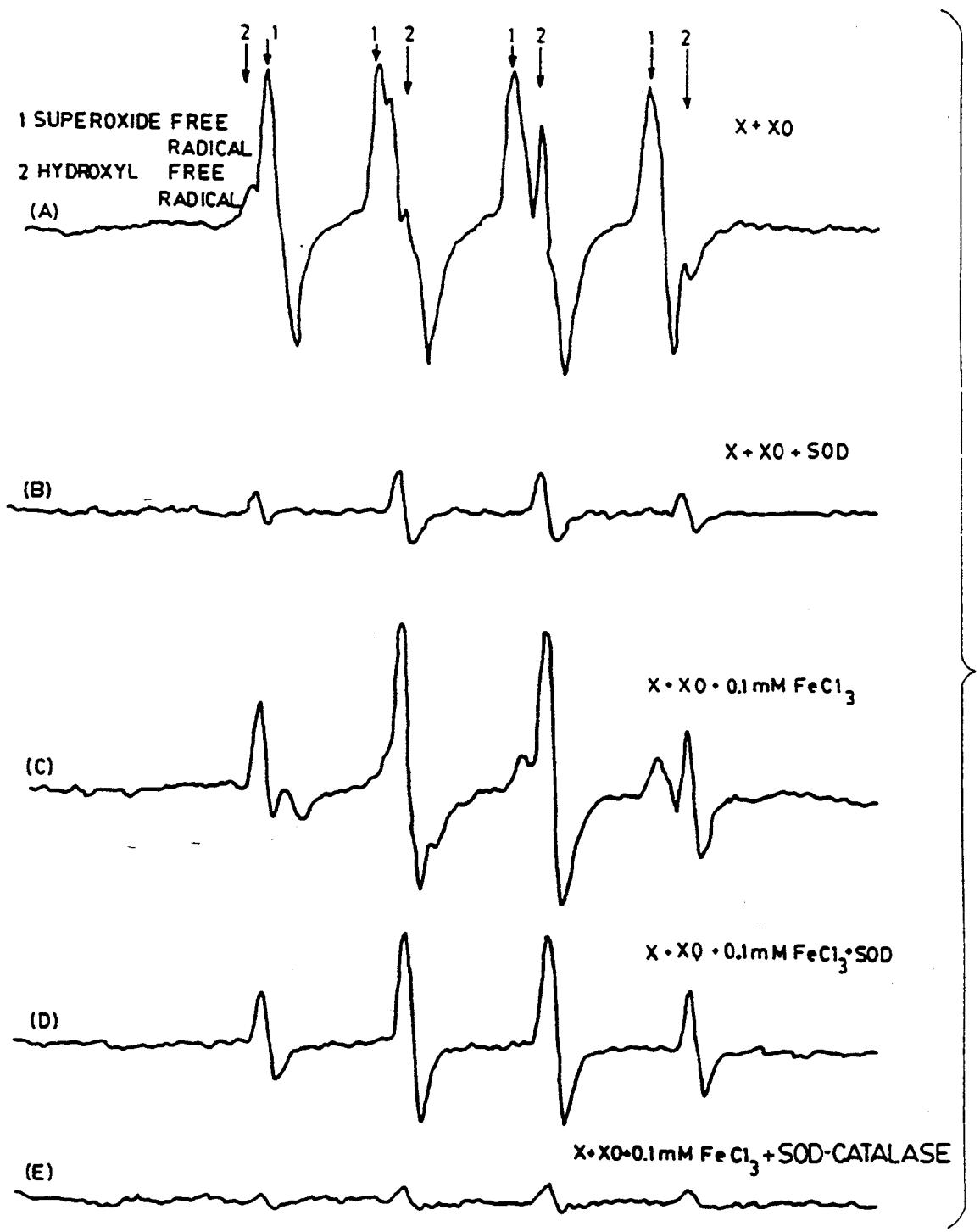
FIGS. 2a–2e show scavenging of oxygen free radicals and hydroxyl free radicals under various conditions: Panel A—control; Panel B—addition of SOD; Panel C—addition of 0.1 mM $FeCl_3$; Panel D—addition of SOD+0.1 mM $FeCl_3$; Panel E—addition of SOD-catalase conjugate+0.1 mM $FeCl_3$. Radicals detected by Electron Paramagnetic Resonance (EPR) spin trapping, peaks scored on an intensity scale of 16 (Bruker 300).

Replicate samples were treated as shown in the panels of FIG. 2 and resultant free radical levels were measured by EPR as described in Example 5. FIG. 2 shows the results of this experiment.

Panel A shows generation of superoxide free radicals and hydroxyl free radicals in the absence of further additions to the reaction mixture. Addition of SOD gave scavenging of virtually all oxygen free radicals but left some hydroxyl free radical unscavenged (Panel B). Addition of 0.1 mM $FeCl_3$ greatly diminished the O. signal while stimulating the OH. signal (Panel C).

Addition of SOD along with 0.1 mM $FeCl_3$ (for up to 2 h) did little to remove the increased OH. radical (Panel D) whereas addition of SOD-catalase conjugate virtually eliminated the iron-stimulated OH. radical.

Increasing doses of SOD had no effect on the size of the OH. signal except at higher iron concentrations where the OH. signal was then increased with increasing SOD due to the iron and the generation of $H_2O_2$.

Example 7

Figure 3:
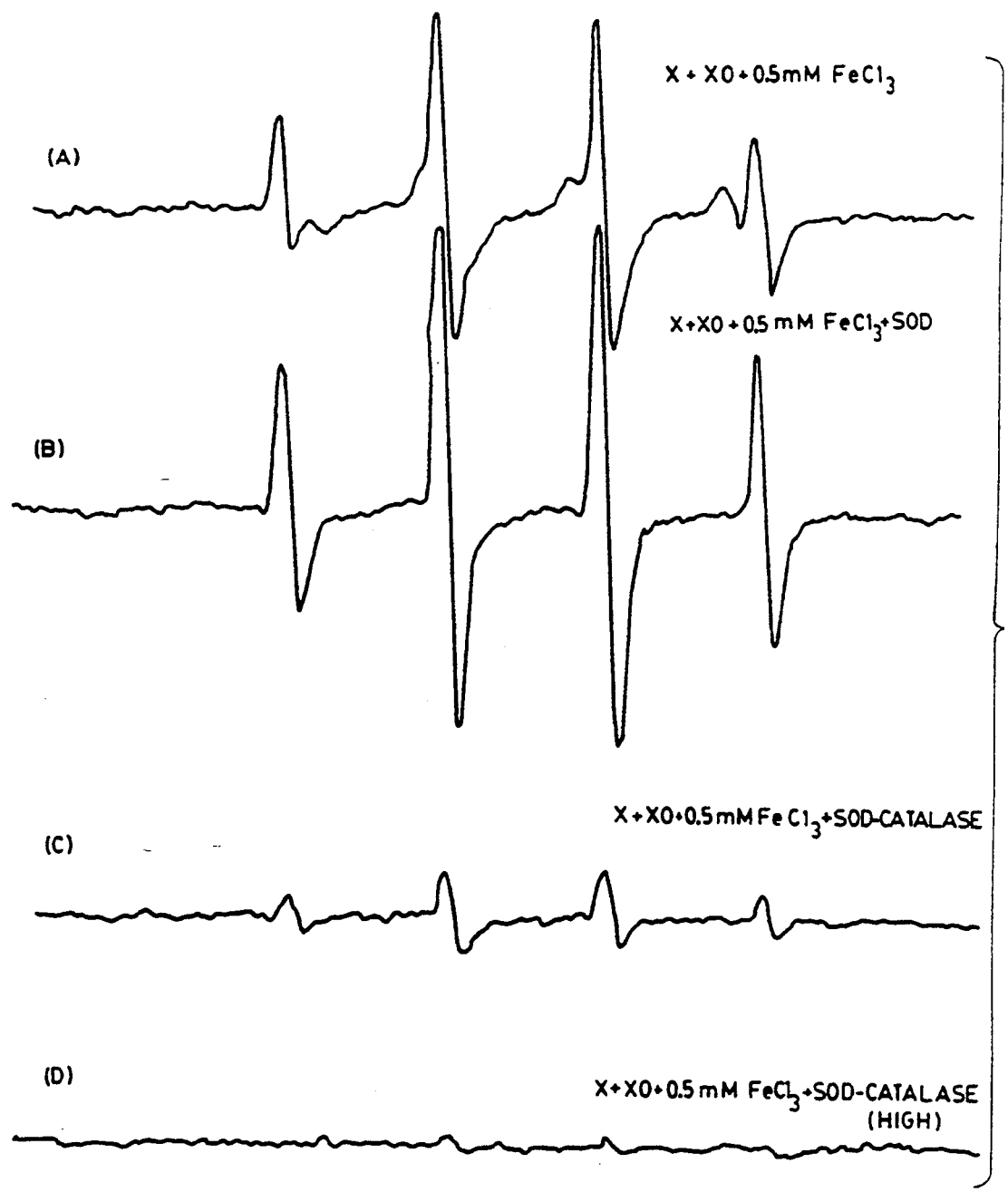
FIGS. 3a–3d show scavenging of hydroxyl free radicals under various conditions: Panel A—in presence of 0.5 mM $FeCl_3$; Panel B—in presence of SOD+0.5 mM $FeCl_3$; Panels C & D—in presence of low and high levels of SOD-catalase conjugate+0.5 mM $FeCl_3$. Radicals detected as in FIG. 2.

The experiment of Example 6 was repeated using 0.5 mM $FeCl_3$ +SOD-catalase conjugate prepared as in Example 1, and the results are shown in FIG. 3. As seen in Panel A, in the presence of 0.5 mM $FeCl_3$ only OH. was readily discerned. The iron assured conversion of the O. to OH. via the Haber-Weiss reaction. The addition of SOD to the reaction further stimulated OH. production (Panel B) presumably by the action of $H_2O_2$. This indicates the potential toxicity of SOD alone, in that it actually generates the more toxic OH free radical species. Panels C and D show that addition of SOD-catalase conjugates, (500 Units and 2000 Units (high) SOD respectively) completely removed OH. radical even in the presence of 0.5 mM $FeCl_3$.

Example 8

The experimental set up of Example 7 was used to compare the scavenging effect of SOD alone, mixtures of unconjugated SOD and catalase and SOD-catalase conjugates (prepared as in Example 1), on OH. radical levels stimulated by 0.1 mM $FeCl_3$. Results are shown in Table 3.

TABLE 3

| Incubation Conditions | Integrated OH. free radical values* (%) |
|---|---|
| 1. x + xo + 0.1mM $FeCl_3$ + SOD (42.4μ) | 100 |
| 2. x + xo + 0.1mM $FeCl_3$ + SOD (84.8μ) | 100 |
| 3. x + xo + 0.1mM $FeCl_3$ + SOD (127μ) | 100 |
| 4. x + xo + 0.1mM $FeCl_3$ + SOD (42.4μ) + CAT (6μ) | 80 |
| 5. x + xo + 0.1mM $FeCl_3$ + SOD-CAT (units as in 4) | 62 |
| 6. x + xo + 0.1mM $FeCl_3$ + SOD (84.8μ) + CAT (12μ) | 36 |
| 7. x + xo + 0.1mM $FeCl_3$ + SOD-CAT (units as in 6) | 22 |
| 8. x + xo + 0.1mM $FeCl_3$ + SOD (127μ) + CAT (18μ) | 26 |
| 9. x + xo + 0.1mM $FeCl_3$ + SOD-CAT (units as in 8) | 0–5** |

*1 set as 100%
**large error due to very low values
x = xanthine and xo = xanthine oxide Samples 1, 2 and 3 showed that in the presence of iron and SOD, substantial amounts of OH free radical formed which were not abolished by increasing SOD levels. Catalase in the presence of SOD (Samples 4,6 and 8) decreased OH free radical formed, probably by decreasing $H_2O_2$.

In each case, it is seen that comparable levels of catalase conjugated to SOD (5,7 and 9) were more effective than free SOD and Catalase (4,6 and 8) presumably because $H_2O_2$ formed by SOD was immediately converted to $H_2O+O_2$ by the conjugated catalase thus inhibiting the formation of OH free radicals by the Haber Weiss reaction.

SOD and catalase in conjugated form were more effective in scavenging free radicals than similar levels of the two enzymes in unconjugated form.

Example 9

A hanging working rat heart model of ischemia-reperfusion was set up as described by Lopaschuk et el., Circulation Research (1988), Vol. 63, p. 1036.

A 10 min Langendorff perfusion was initiated with Krebs-Henseliet buffer (pH 7.5) containing 11 mM glucose. Hearts were then switched to the working mode for 10 min with buffer containing 3% bovine serum albumin, 11 mM glucose and 1.2 mM palmirate. Hearts were perfused at a left atrial filling pressure of 11.5 mm Hg and a hydrostatic afterload of 80mm Hg.

When used, SOD and SOD-careless conjugate were added directly to the perfusate. Low dose SOD=100 U/ml; high dose SOD=1000 U/ml; for conjugates, same amounts of SOD were conjugated to a constant amount of catalase, the conjugate being prepared as in Example 1.

Aerobic work continued under these conditions for an additional 10 min. The preload and afterload lines were then clamped inducing global ischemia. Following 30 min of global ischemia, the hearts were reperfused for 30 min then frozen with Wollenberger clamps cooled to the temperature of liquid nitrogen.

Cardiac function was measured as described by Lopaschuk etal.

The results are shown in Table 4 and FIGS. 4a to 4d.

TABLE 4
CARDIAC FUNCTION

| Experimental Group | % Return to Base following ischemia |
|---|---|
| Control | 32 |
| Low Dose SOD | 48 |
| High Dose SOD | 20 (0-50)* |
| Low Dose SOD-Catalase | 80 |
| High Dose SOD-Catalase | 80** |

Each value represents the mean from at least 6 hearts.
*The range for the high SOD hearts was much larger than any of the others and of a total of 10 hearts there were 4 complete failures.
**The value for the High SOD-Catalase is from only 4 hearts.

As seen from Table 4, the lower dose of SOD gave significant protection compared to the control, but the higher SOD dose was very toxic to the heart preparation. When the lower dose of SOD was conjugated to catalase, the conjugate was much more protective of heart function than the equivalent amount of free SOD. A similar degree of protection was seen with the conjugate containing the high SOD dose, the additional toxicity seen with that level of SOD alone being completely eliminated.

Figure 4A:
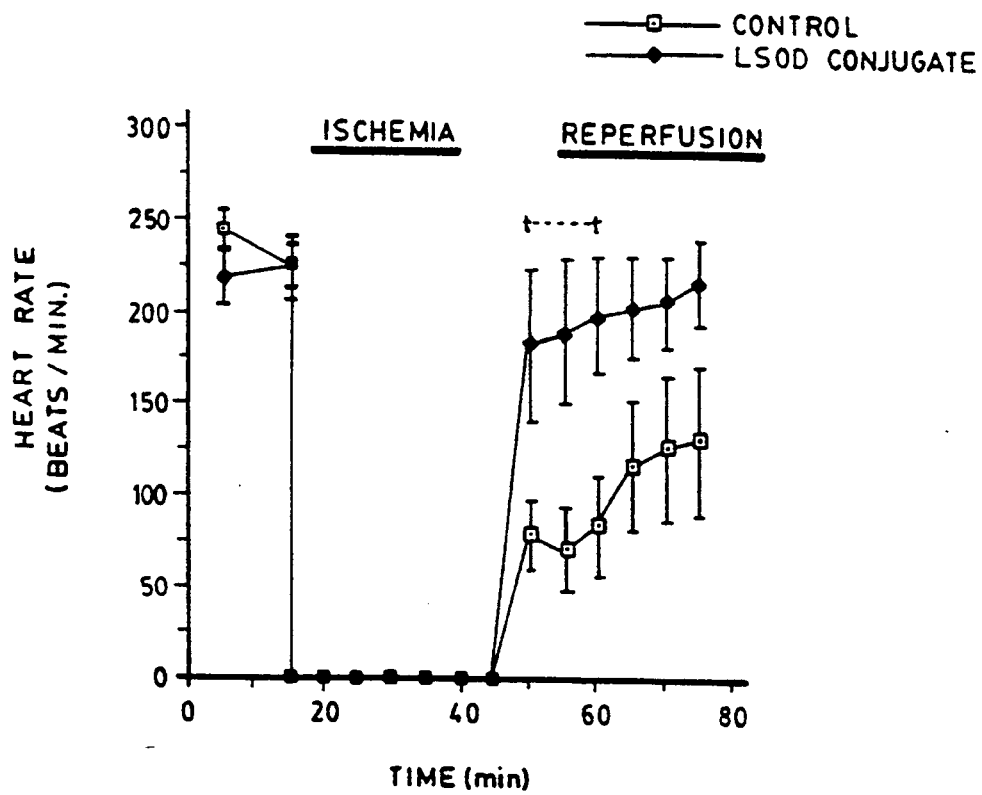
FIGS. 4a–4d shows the effect of SOD-catalase conjugate on rat heart function after ischaemia: (a), (b) and (c)—comparisons of SOD-catalase conjugate and control; (d)—comparison of SOD-catalase conjugate and SOD alone.
Figure 4B:
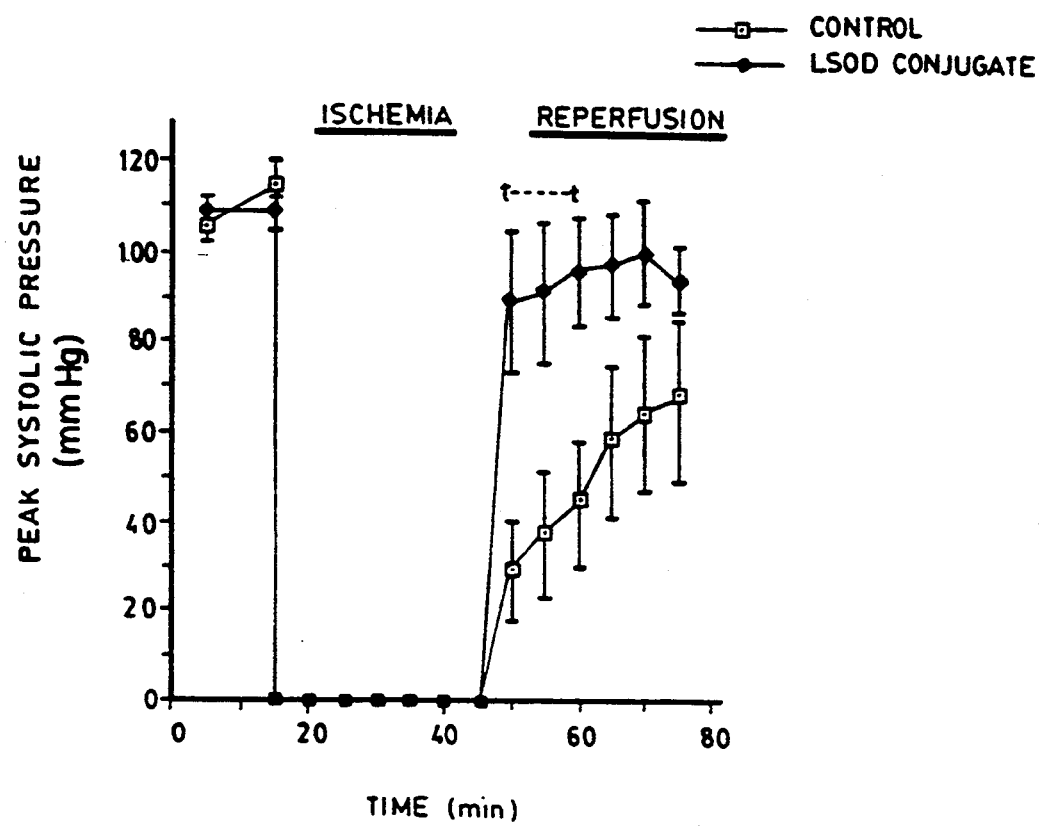
Figure 4C:
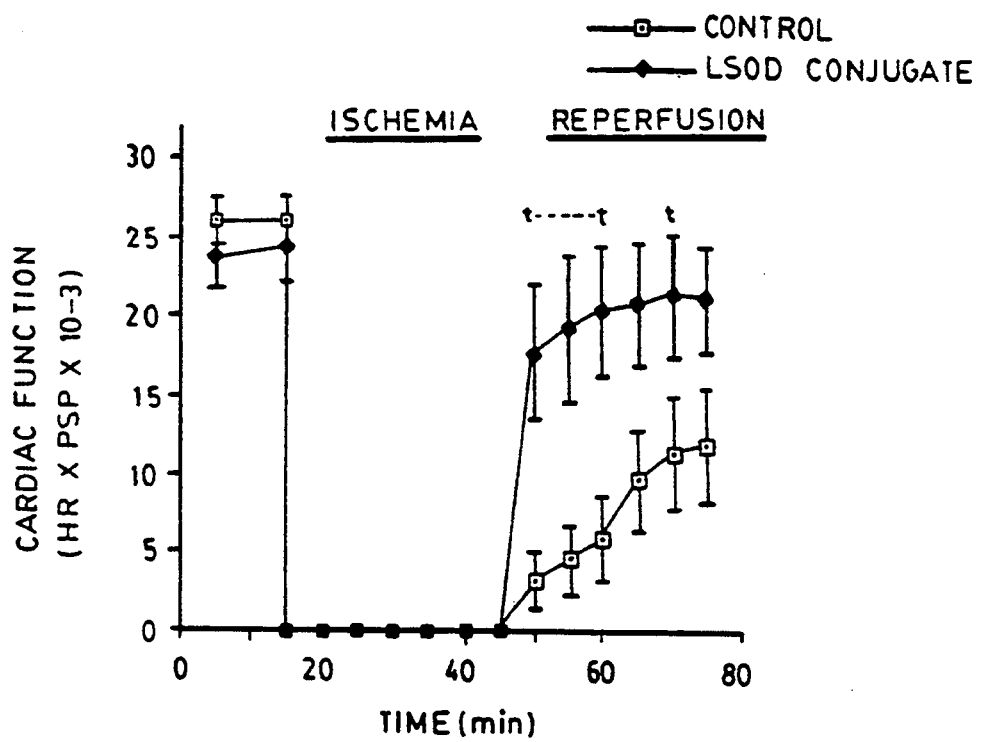
Figure 4D:
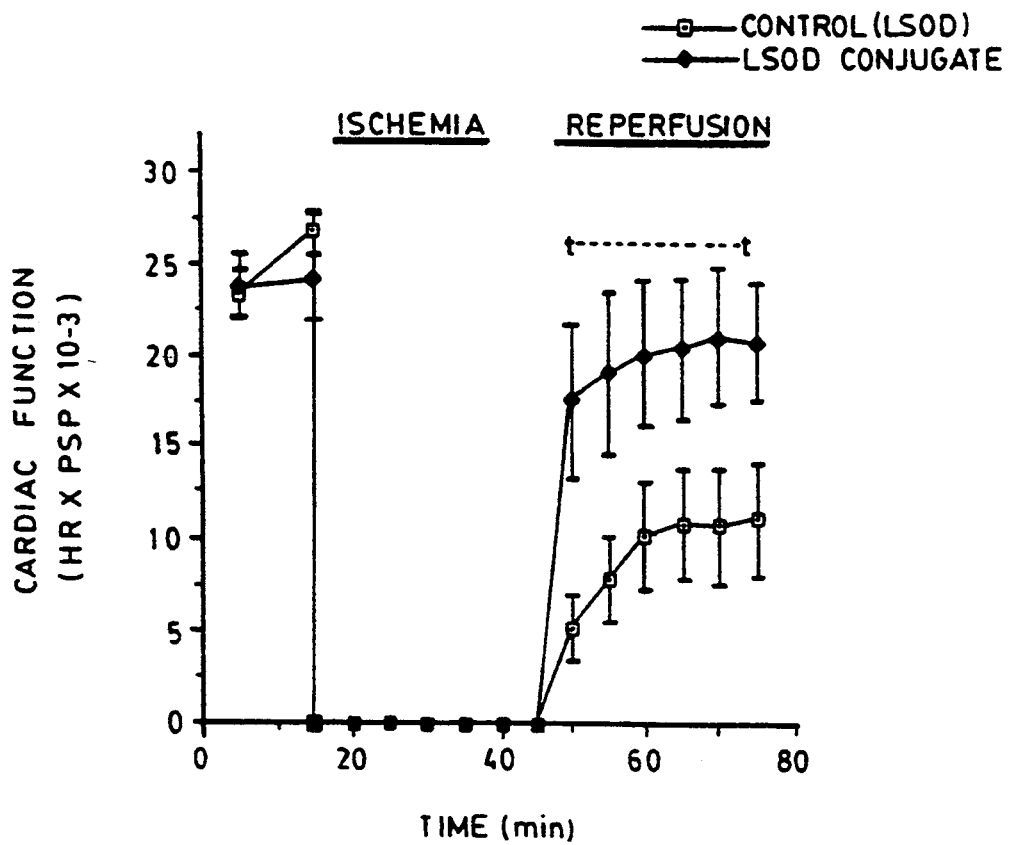

FIGS. 4a to 4c show the protective effect of low dose SOD-catalase conjugates compared with control perfusses. FIG. 4d shows the improved protective effect of low dose SOD-catalase conjugate compared with an equivalent low dose of SOD alone.

SOD-catalase conjugates clearly permitted restoration of heart function to a much greater level after ischemia than SOD alone. The SOD-conjugate had a molecular weight of 450,000±50,000 and was cleared in vivo at a rate 50-100 times more slowly than the equivalent amount of free SOD.

The present invention is not limited to the features of the preferred embodiments described herein, but includes all variations and modifications within the scope of the claims.

We claim:

1. A multi-component conjugate comprising superoxide dismutase linked to catalase.

2. A multi-component conjugate in accordance with claim 1, wherein said conjugate is further linked to albumin.

3. A multi-component conjugate in accordance with claim 1, wherein said conjugate is further linked to an antibody.

4. A multi-component conjugate in accordance with claim 3, wherein said antibody is a monoclonal antibody to heavy chain myosin.

5. A multi-component conjugate in accordance with claim 1, wherein said conjugate is chemically linked by a linking group selected from the group consisting of glutaraldehyde and carbodiimide.

6. A multi-component conjugate according with claim 1, wherein said conjugate has a molecular weight in the range of about 200,000 to about 1,200,000 and a mole ratio of superoxide dismutase to catalase in the range of about 1:1 to about 8:1.

7. A pharmaceutical composition comprising a multi-component conjugate comprising superoxide dismutase linked to catalase.

* * * * *